United States Patent
Fung et al.

(10) Patent No.: US 8,221,984 B2
(45) Date of Patent: Jul. 17, 2012

(54) BIOMARKERS FOR OVARIAN CANCER

(75) Inventors: Eric T. Fung, Los Altos, CA (US);
Robert Bast, Houston, TX (US);
Vladimir Podust, Castco, CA (US);
Charlotte Clarke, Seabrook, TX (US)

(73) Assignees: Vermillion, Inc., Austin, TX (US);
Board of Regents, The University of Texas System, Austin, TX (US)

( * ) Notice: Subject to any disclaimer, the term of this patent is extended or adjusted under 35 U.S.C. 154(b) by 49 days.

(21) Appl. No.: 12/079,592

(22) Filed: Mar. 27, 2008

(65) Prior Publication Data

US 2009/0170208 A1 Jul. 2, 2009

Related U.S. Application Data

(60) Provisional application No. 60/920,274, filed on Mar. 27, 2007, provisional application No. 61/034,469, filed on Mar. 6, 2008.

(51) Int. Cl.
*G01N 33/53* (2006.01)

(52) U.S. Cl. ....................................................... 435/7.1

(58) Field of Classification Search .................... None
See application file for complete search history.

(56) References Cited

U.S. PATENT DOCUMENTS

| | | | |
|---|---|---|---|
| 6,335,170 | B1 | 1/2002 | Orntoft |
| 2005/0059013 | A1 | 3/2005 | Chan et al. |
| 2007/0087448 | A1 | 4/2007 | Nelsestuen |
| 2007/0172902 | A1 | 7/2007 | Zhang et al. |
| 2008/0274481 | A1 | 11/2008 | Fung |
| 2010/0197561 | A1 | 8/2010 | Fung |

FOREIGN PATENT DOCUMENTS

| | | |
|---|---|---|
| WO | WO-02/097438 A1 | 12/2002 |
| WO | WO-2005/005601 A2 | 1/2005 |
| WO | WO-2006/019906 A1 | 2/2006 |
| WO | WO-2006/099126 A2 | 9/2006 |
| WO | WO-2007/002264 A2 | 1/2007 |
| WO | WO-2007/002527 A2 | 1/2007 |
| WO | WO-2008/048508 A2 | 4/2008 |

OTHER PUBLICATIONS

Huhtala et al (Int J Cancer, 1983, 31(6): Abstract).*
Stenman et al (Scand J Clin Lab Invest Suppl, 1991, 207: Abstract).*
Cole et al (The Yale Journal of Biology and Medicine, 1989, 62: 367-378).*
Schaub et al (Kidney International, 2004, 65: 323-332).*
Halila et al (Br J Cancer, 1988, 57: 304-307).*
Tockman et al (Cancer Res., 1992, 52:2711s-2718s).*
Yasui Wataru et al., Search for new biomarkers of gastric cancer through serial analysis of gene expression and its clinical implications. Cancer Science May 2004, vol. 95(5), pp. 385-392.
Yoneda et al., "Expression of Angiogenesis-Related Genes and progression of Human Ovarian Carcinomas in Nude Mice", Journal of National Cancer Institute, Mar. 1998, vol. 90(6), pp. 447-454.
Zhang et al., "Three Biomarkers identified from Serum Proteomic Analysis for the Detection of Early Stage Ovarian Cancer", Cancer Research, vol. 64(16), Aug. 2004, pp. 5882-5890.
Office Action dated May 16, 2008, for related European Application No. 06785526.2.
European Search Report dated Apr. 14, 2009, for related European Patent Application No. 06773938.3.
International Search Report dated Jun. 1, 2009, for related application PCT/US2008/012323.
International Search Report dated Sep. 11, 2008, for related application PCT/US07/21867.
St. Swierzko A. et al. "Mannan-binding lectin (MBL) in women with tumours of the reproductive system." Cancer Immunol Immunother. Jul. 2007;56(7):959-71.
European Search Report mailed Feb. 15, 2011 for PCT/US2008/004088 (EP 08 77 9577).
Berbee et al., "Severe hypertriglyceridemia in human APOC1 transgenic mice is caused by apoC-I-induced inhibition of LPL." Journal of Lipid Research, vol. 46(2), pp. 297-306, (2005).
Hampel D J, et al., Toward Proteomics in Uroscopy: urinary Protein Profiles after Radiocontrast Medium Administration, Journal of the American Society of Nephrology, vol. 12(5), May 2001, pp. 1026-1035.
Hoffmann et al., "Immunofluorometric Quantitation and Histochemical localisation of Kallikrein 6 Protein in Ovarian Cancer Tissue: A new independent unfavourable prognostic biomarker", British Journal of Cancer, Nature, vol. 87(7), 2002, pp. 763-771.
Kikuchi et al., "Significance of Serum Tumor Markers in Patients with Carcinoma of the Ovary", Obstetrics and Gynecology, vol. 63(4), Apr. 4, 1984, pp. 561-566.
Kim et al., "Osteopontin as a potential diagnostic biomarker for ovarian cancer", JAMA, vol. 287(13), Apr. 3, 2002, pp. 1671-1679.
Kozak et al., "Characterization of serum biomarkers for detection of early stage ovarian cancer", Proteomics 2005, vol. 5, 2005, pp. 4589-4596.
Lin et al., "Plasma proteomic pattern as biomarkers for ovarian cancer", Int. J. Gynecol Cancer, vol. 16, 2006, pp. 139-146.
Tockman et al., "Considerations in Bringing a Cancer Biomarker to Clinical Application", Cancer Research vol. 52, 1992, pp. 2711s-2718s.
Trope C G et al., "$\beta_2$—microglobulin: A tumor marker of gynecologic cancer", American Journal of Obstetrics and Gynecology 1980, vol. 137(6), 1980, pp. 743-744.
Carr S. et al. The need for guidelines in publication of peptide and protein identification data: Working Group on Publication Guidelines for Peptide and Protein Identification Data. Mol Cell Proteomics. Jun. 2004;3(6):531-3.

* cited by examiner

*Primary Examiner* — Sean Aeder

(74) *Attorney, Agent, or Firm* — Edwards Wildman Palmer LLP; Peter F. Corless; Andrew W. Shyjan, Esq.

(57) ABSTRACT

The present invention provides protein-based biomarkers and biomarker combinations that are useful in qualifying ovarian cancer status in a patient. In particular, it has been found that the biomarkers set forth in Table 1 are biomarkers for ovarian cancer. The biomarkers can be detected by SELDI mass spectrometry.

9 Claims, No Drawings

BIOMARKERS FOR OVARIAN CANCER

This application claims the benefit of U.S. Provisional Application No. 60/920,274, filed Mar. 27, 2007 and U.S. Provisional Application No. 61/034,469, filed Mar. 6, 2008. The entire contents of each of the aforementioned applications is hereby incorporated herein by reference.

FIELD OF THE INVENTION

The invention relates generally to clinical diagnostics.

BACKGROUND OF THE INVENTION

Ovarian cancer is among the most lethal gynecologic malignancies in developed countries. Annually in the United States alone, approximately 23,000 women are diagnosed with the disease and almost 14,000 women die from it. (Jamal, A., et al., CA Cancer J. Clin, 2002; 52:23-47). Despite progress in cancer therapy, ovarian cancer mortality has remained virtually unchanged over the past two decades. (Id.) Given the steep survival gradient relative to the stage at which the disease is diagnosed, early detection remains the most important factor in improving long-term survival of ovarian cancer patients.

The poor prognosis of ovarian cancer diagnosed at late stages, the cost and risk associated with confirmatory diagnostic procedures, and its relatively low prevalence in the general population together pose extremely stringent requirements on the sensitivity and specificity of a test for it to be used for screening for ovarian cancer in the general population.

The identification of tumor markers suitable for the early detection and diagnosis of cancer holds great promise to improve the clinical outcome of patients. It is especially important for patients presenting with vague or no symptoms or with tumors that are relatively inaccessible to physical examination. Despite considerable effort directed at early detection, no cost effective screening tests have been developed (Paley P J., Curr Opin Oncol, 2001; 13(5):399-402) and women generally present with disseminated disease at diagnosis. (Ozols R F, et al., Epithelial ovarian cancer. In: Hoskins W J, Perez C A, Young R C, editors. Principles and Practice of Gynecologic Oncology. 3rd ed. Philadelphia: Lippincott, Williams and Wilkins; 2000. p. 981-1057).

The best-characterized tumor marker, CA125, is negative in approximately 30-40% of stage I ovarian carcinomas and its levels are elevated in a variety of benign diseases. (Meyer T, et al., Br J Cancer, 2000; 82(9):1535-8; Buamah P., J Surg Oncol, 2000; 75(4):264-5; Tuxen M K, et al., Cancer Treat Rev, 1995; 21(3):215-45). Its use as a population-based screening tool for early detection and diagnosis of ovarian cancer is hindered by its low sensitivity and specificity. (MacDonald N D, et al., Eur J Obstet Gynecol Reprod Biol, 1999; 82(2):155-7; Jacobs I, et al., Hum Reprod, 1989; 4(1):1-12; Shih I-M, et al., Tumor markers in ovarian cancer. In: Diamandis E P, Fritsche, H., Lilja, H., Chan, D. W., and Schwartz, M., editor. Tumor markers physiology, pathobiology, technology and clinical applications. Philadelphia: AACC). Although pelvic, and more recently, vaginal sonography has been used to screen high-risk patients, neither technique has sufficient sensitivity and specificity to be applied to the general population. (MacDonald N D, et al., supra). Recent efforts in using CA125 in combination with additional tumor markers (Woolas R P X F, et al., J Natl Cancer Inst, 1993; 85(21): 1748-51; Woolas R P, et al., Gynecol Oncol, 1995; 59(1): 111-6; Zhang Z, et al., Gynecol Oncol, 1999; 73(1): 56-61; Zhang Z, et al., Use of Multiple Markers to Detect Stage I Epithelial Ovarian Cancers: Neural Network Analysis Improves Performance. American Society of Clinical Oncology 2001; Annual Meeting, Abstract) in a longitudinal risk of cancer model (Skates S J, et al., Cancer, 1995; 76(10 Suppl): 2004-10), and in tandem with ultrasound as a second line test (Jacobs I D A, et al., Br Med J, 1993; 306(6884): 1030-34; Menon U TA, et al., British Journal of Obstetrics and Gynecology, 2000; 107(2): 165-69) have shown promising results in improving overall test specificity, which is critical for a disease such as ovarian cancer that has a relatively low prevalence. See also Menon et al. J. Clin. Oncology (2005) 23(31): 7919-26.

Due to the dismal prognosis of late stage ovarian cancer, it is the general consensus that a physician will accept a test with a minimal positive predictive value of 10%. (Bast, R. C., et al., Cancer Treatment and Research, 2002; 107:61-97). Extending this to the general population, a general screening test would require a sensitivity greater than 70% and a specificity of 99.6%. Currently, none of the existing serologic markers, such as CA125, CA72-4, or M-CSF, individually delivers such a performance. (Bast, R. C., et al., Int J Biol Markers, 1998; 13:179-87).

Thus, there is a critical need for new serological markers that individually or in combination with other markers or diagnostic modalities deliver the required sensitivity and specificity for early detection of ovarian cancer. (Bast R C, et al., Early detection of ovarian cancer: promise and reality. Ovarian Cancer: ISIS Medical Media Ltd., Oxford, UK).

Given the low incidence of ovarian cancer, a screening test intended for the asymptomatic woman with adequate positive predictive remains elusive. It has been demonstrated, however, that even in the absence of a general screening test, one factor that does improve long-term survival of patients with ovarian cancer is appropriate triage to the specialist gynecologic oncologist (Craig, CC et al, Effect of surgeon specialty on processes of care and outcomes for ovarian cancer patients, J Natl Canc Inst, 2006: 98, 172-80). This is particularly true of women who present to their physician with symptoms suggestive of a pelvic mass.

Thus, it is desirable to have a reliable and accurate method of determining the ovarian cancer status in patients, the results of which can then be used to manage subject treatment.

SUMMARY OF THE INVENTION

It has been found that the biomarkers identified in Table 1 are biomarkers for ovarian cancer. Put another way, increased or decreased levels (see Table 1) of the biomarkers identified in Table 1 are correlated with ovarian cancer.

In certain embodiments, the disease statuses to be distinguished are: ovarian cancer versus benign ovarian disease; ovarian versus other malignancy (e.g., breast cancer or colon cancer); stage I ovarian cancer versus non-ovarian cancer; and recurrence of ovarian cancer versus non-ovarian cancer; early versus late ovarian cancer. Based on the status determined, further procedures may be indicated, including additional diagnostic tests or therapeutic procedures or regimens.

Moreover, when one or more of the biomarkers identified in Table 1 are used in combination with the level of other biomarkers, the predictive power of the diagnostic test can be improved. More specifically, increased levels of the biomarkers of the invention and abarent levels of other known cancer markers can be used in diagnostic tests of the invention.

In one aspect, the present invention provides methods for qualifying ovarian cancer status in a subject comprising measuring one or more biomarkers in a biological sample from the subject, wherein at least one biomarker is selected the biomarkers set forth in Table 1, and correlating the measurement or measurements with an ovarian cancer status selected from ovarian cancer and non-ovarian cancer. In one embodiment of such methods, a plurality of biomarkers in Table 1 are measured. In a further aspect of such methods, a plurality of biomarkers in the biological sample are measured, wherein the measured biomarkers further comprise in addition to the one or more biomarkers identified in Table 1, at least two known biomarkers.

In another embodiment, one or more biomarkers are measured by mass spectrometry. The mass spectrometry suitably may be SELDI-MS. In a further aspect, one or more biomarkers are measured by immunoassay.

A variety of biological samples may be employed in methods of the invention, including e.g. where the biological sample comprises blood or a blood derivative, or where the biological sample comprises ovarian cyst fluid, ascites, or urine. In a preferred embodiment, the biological sample is urine.

In one embodiment of methods of the invention, wherein non-ovarian cancer is benign ovarian disease. In another embodiment, non-ovarian cancer is a gynecological condition such as benign ovarian cyst, endometriosis, uterine fibroma, breast cancer and cervical cancer. In a further embodiment, the ovarian cancer is stage I or II ovarian cancer. In certain aspects, the subject has been treated for ovarian cancer and the ovarian cancer is recurrence of cancer.

Methods of the invention may further comprises reporting the status to the subject, recording the status on a tangible medium, and/or managing subject treatment based on the status. One or more biomarker may be after subject management and the measurement correlated with disease progression.

In a preferred aspect, methods are provided for determining the course of ovarian cancer comprising (a) measuring, at a first time, one or more biomarkers in a biological sample from the subject, wherein at least one biomarker is selected from the biomarkers set forth in Table 1; (b) measuring, at a second time, the same at least one biomarker is selected from the group consisting of biomarkers set forth in Table 1 in a biological sample from the subject; and (c) comparing the first measurement and the second measurement; wherein the comparative measurements determine the course of the ovarian cancer.

In another embodiment, the invention provides a kit that comprises (a) a solid support comprising at least one capture reagent attached thereto, wherein the capture reagent binds one or more biomarkers selected from the group consisting of biomarkers set forth in Table 1; and (b) instructions for using the solid support to detect the one or more biomarkers. The solid support may comprise e.g. a SELDI probe. The kit also may optionally comprise a standard reference of one or more biomarkers selected from the group consisting of biomarkers set forth in Table 1.

In a yet further embodiment, the invention provides a kit that comprises (a) at least one solid support comprising at least one capture reagent attached thereto, wherein the capture reagent or reagents bind one or more biomarkers selected from the group consisting of biomarkers set forth in Table 1 and at least one of known biomarker, e.g., ApoA1, transferrin, CTAP III and ITIH4 fragment; and (b) instructions for using the solid support or supports to detect one or more biomarkers selected from the group consisting of biomarkers set forth in Table 1 and at least one of the known biomarkers. The solid support may comprise e.g. a SELDI probe.

The invention further includes software products that comprise (a) code that accesses data attributed to a sample, the data comprising measurement of at least one biomarker in the sample, wherein at least one biomarker is selected from the group consisting of the biomarkers set forth in Table 1; and (b) code that executes a classification algorithm that classifies the ovarian cancer status of the sample as a function of the measurement.

The invention also provides methods comprising communicating to a subject a diagnosis relating to ovarian cancer status determined from the correlation of at least one biomarker in a sample from the subject, wherein at least one biomarker is selected from the group consisting of the biomarkers set forth in Table 1. The diagnosis may be suitably communicated to the subject e.g. via a computer-generated medium.

The invention further provides methods for identifying a compound that interacts with one or more biomarkers set forth in Table 1, wherein said method comprises a) contacting one or more biomarkers biomarkers set forth in Table 1 with a test compound; and b) determining whether the test compound interacts with one or more biomarkers selected biomarkers set forth in Table 1.

Other aspects of the invention are discussed infra.

DETAILED DESCRIPTION OF THE INVENTION

1. Introduction

A biomarker is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. As such, they are useful as markers for disease (diagnostics), therapeutic effectiveness of a drug (theranostics) and of drug toxicity.

Biomarkers of this invention were discovered using SELDI. Accordingly, they are characterized, in part, by their mass-to-charge ratio, the shape of the peak in a mass spectrum and their binding characteristics. These characteristics represent inherent characteristics of the biomolecule and not process limitations in the manner in which the biomolecule is discriminated.

Biomarkers of this invention are characterized in part by their mass-to-charge ratio. The mass-to-charge ratio of each biomarker is provided herein. A particular molecular marker designated, for example, as "M2789" has a measured mass-to-charge ratio of 2789 D. The mass-to-charge ratios were determined from mass spectra generated on a Ciphergen Biosystems, Inc. PBS II mass spectrometer or a Ciphergen PCS 4000 mass spectrometer. The PBS II is instrument has a mass accuracy of about +/−0.15 percent. Additionally, the instrument has a mass resolution of about 400 to 1000 m/dm, where m is mass and dm is the mass spectral peak width at 0.5 peak height. The PCS4000 instrument has a mass accuracy of about +/−0.12% raw data with an expected externally calibrated mass accuracy of 0.1% and internally calibrated mass accuracy of 0.01%. Additionally, the instrument has a mass resolution of about 1000 to 2000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII or PCS4000, taking the maximum and minimum mass-to-charge-ratio in the cluster, and dividing by two. Accordingly, the masses provided reflect these specifications.

Biomarkers of this invention are further characterized by the shape of their spectral peak in time-of-flight mass spectrometry.

2. Biomarkers for Ovarian Cancer

Specific biomarkers thus discovered are presented in Table 1. The "ProteinChip assay" column refers to chromatographic fraction in which the biomarker is found, the type of biochip to which the biomarker binds and the wash conditions, as per the Examples. In each case, the biomarkers each may be found using a variety of alternate ProteinChip assays.

TABLE 1

| Marker | P value | Up- or down-regulation in cancer | m/z (MW for identified biomarkers) |
|---|---|---|---|
| M1719 | 4.90E−11 | Down | 1719.775447 |
| M1992 | 2.19E−17 | Down | 1992.056066 |
| M2007 | 1.39E−19 | Down | 2007.29413 |
| M2026 | 2.60E−18 | Down | 2026.263783 |
| M2126 | 3.42E−19 | Down | 2126.32397 |
| M2211 | 2.38E−17 | Down | 2211.015382 |
| M2259 | 2.19E−14 | Down | 2259.609232 |
| M2300 | 6.26E−14 | Down | 2300.04461 |
| Hepcidin 22 | 8.51E−11 | Up | 2436.07 |
| Hepcidin 25 | 2.62E−12 | Up | 2789.41 |
| M3018 | 4.43E−13 | Down | 3018.066325 |
| M3043 | 6.58E−15 | Down | 3043.297332 |
| Neutrophil defensin 2 | .00162 | Down | 3371.01 |
| Neutrophil defensin 1 | .00224 | Down | 3442.09 |
| M3262 | 5.04E−10 | Down | 3262.096586 |
| Collagen alpha-1(I) fragment | 7.95E−29 | Up | 3721.88 |
| Albumin fragment | 2.73E−15 | Up | 4355.82 |
| Albumin fragment | 1.08E−19 | Up | 4417.02 |
| Fibrinogen beta, N-terminal fragment | 1.08E−19 | Up | 4417.85 |
| Beta defensin 1 | 1.8E−4 | Up | 4750.50 |
| Small MBL-associated protein, C-terminal fragment (sMAP) | 4.35E−6 | Up | 5499.04 |
| Pancreatic secretory trypsin inhibitor (PSTI) | 9.33E−05 | Up | 6241.04 |
| M6331 | 5.96E−13 | Up | 6331.460679 |
| Ubiquitin, C-terminal truncation | 0.00566 | Up | 8181.39 |
| Ubiquitin, C-terminal truncation | 1.47E−17 | Up | 8294.55 |

TABLE 1-continued

| Marker | P value | Up- or down-regulation in cancer | m/z (MW for identified biomarkers) |
|---|---|---|---|
| Ubiquitin | 4.20E−17 | Up | 8564.84 |
| Anti-neoplastic Urinary protein | .0292 | Up | 8843.16 |
| Saposin B, glycosylated | 5.66E−8 | Up | 9072.44 |
| M9616 | 7.62E−14 | Up | 9616.842953 |
| Saposin B, glycosylated | | | 9746.07 |
| LTBP-2, C-terminal fragment | 9.48E−4 | Up | 9873 |
| LTBP-2, C-terminal fragment | 1.00E−26 | Up | 10207 |
| M10559 | 8.29E−10 | Up | 10559.03627 |
| Beta-2-microglobulin | 9.03E−24 | Up | 11729.17 |
| Trefoil factor 2 | 4.49E−4 | Up | 11975.48 |
| M16973 | 1.63E−13 | Up | 16973.5595 |
| Ig kappa | 1.15E−10 | Up | 23524.04157 |

Hepcidin

Hepcidin was originally identified as a 25 amino acid peptide (hepcidin-25) in human plasma and urine, exhibiting antimicrobial activity. The full-length hepcidin precursor is an 84 amino acid protein (SwissProt Accession No. P81172) comprising a signal sequence and a pro-region (see Kulaksiz, H. et al. (2004) Gut 53:735-743). The hepcidin biomarkers of the present invention are derived from the C-terminus of the full-length hepcidin protein.

```
Hepcidin 25 MW 2789.41
                            (SEQ ID NO: 1)
DTHFPICIFCCGCCHRSKCGMCCKT Hepcidin 22 MW 2436.07
                            (SEQ ID NO: 2)
FPICIFCCGCCHRSKCGM CCKT
```

Ubiquitin

Ubiquitin is a 76 amino acid polypeptide (SwissProt #P62988). The biomarkers of the ubiquitin biomarkers of the present invention comprise full length ubiquitin as well as C-terminal truncations of ubiquitin.

```
(A) full-length ubiquitin (SEQ ID NO: 3),
MW 8564.84 Da
MQIFVKTLTG KTITLEVEPS DTIENVKAKI
QDKEGIPPDQ QRLIFAGKQL
EDGRTLSDYN
IQKESTLHLV LRLRGG (B) truncated Ubiquitin 1 (SEQ ID NO: 4),
MW 8294.55 Da
MQIFVKTLTG KTITLEVEPS
DTIENVKAKI QDKEGIPPDQ
QRLIFAGKQL EDGRTLSDYN
IQKESTLHLV LRL (C) truncated ubiqitin 2 (SEQ ID NO: 5),
MW 8181.39 Da
MQIFVKTLTG KTITLEVEPS DTIENVKAKI
QDKEGIPPDQ QRLIFAGKQL EDGRTLSDYN
IQKESTLHLV LR
```

Beta Defensin 1

Beta defensin 1 is a 68 amino acid polypeptide secreted protein that functions as part of the antimicrobial humoral response in humans (SwissProt #P60022). The beta defensin 1 biomarker of the instant invention is a C-terminal fragment of the full length polypeptide containing 3 disulfide bonds.

```
MW 4750.50 Da
                                        (SEQ ID NO: 6)
LTGLGHRSDH YNCVSSGGQC LYSACPIFTK

IQGTCYRGKA KCCK
```

Neutrophil Defensin

Neutrophil defensin is a 94 amino acid polypeptide that is involved in chemotaxis and immune response in humans (SwissProt #P59665). The neutorphil defensin biomarkers of the invention are C-terminal fragments of the full length polypeptide each containing 3 disulfide bonds.

```
Neutrophil defensin 2 MW 3371.01
                                        (SEQ ID NO: 7)
CYCRIPACIA GERRYGTCIY QGRLWAFCC Neutrophil defensin 1 MW 3442.09
                                        (SEQ ID NO: 8)
ACYCRIPACI AGERRYGTCI YQGRLWAFCC
``` sMAP

Small MBL-associated protein (sMAP) is a 185 amino acid polypeptide (SwissProt #O00187-2). The sMAP biomarker of the invention is a C-terminal fragment of the full length polypeptide with a MW of 5499.04 and contains 3 disulfide bonds and Asn22 is 3-hydroxyasparagine.

```
MW 5499.04 Da
                                        (SEQ ID NO: 9)
EDIDECQVAP GEAPTCDHHC HNHLGGFYCS CRAGYVLHRN

KRTCSEQSL
```

Pancreatic secretory trypsin inhibitor (PSTI) is a 79 amino acid polypeptide (SwissProt #P00995). The PSTI biomarker of the instant invention is a C-terminal fragment of the full length polypeptide that has a MW of 6241.04 and contains 3 disulfide bonds.

```
MW 6241.04
                                        (SEQ ID NO: 10)
DSLGREAKCY NELNGCTKIY DPVCGTDGNT

YPNECVLCFE NRKRQTSILI QKSGPC
```

Anti-Neoplastic Urinary Protein

Anti-neoplastic urinary protein is a 103 amino acid polypeptide (SwissProt #P55000). The anti-neoplastic urinary protein biomarker of the instant invention is a C-terminal fragment of the full length polypeptide that has a MW of 8843.16 and contains 5 disulfide bonds.

```
MW 8843.16
                                        (SEQ ID NO: 11)
LKCYTCKEPM TSASCRTITR CKPEDTACMT

TLVTVEAEYP FNQSPVVTRS CSSSCVATDP

DSIGAAHLIF CCFRDLCNSE L
```

Trefoil Factor 2

Trefoil factor 2 is a 129 amino acid polypeptide (SwissProt #Q03403). The Trefoil factor 2 biomarker of the instant invention is a C-terminal fragment of the full length polypeptide having a MW of 11975.48 and contains 7 disulfide bonds.

```
MW 11975.48
                                        (SEQ ID NO: 12)
EKPSPCQCSR LSPHNRTNCG FPGITSDQCF

DNGCCFDSSV TGVPWCFHPL PKQESDQCVM

EVSDRRNCGY PGISPEECAS RKCCFSNFIF

EVPWCFFPKS VEDCHY
```

Saposin B is a 79 amino acid fragment of the 524 amino acid polypeptide saposin. (SwissProt #P07602). The polypeptide sequence of Saposin B is set forth as SEQ ID NO: 13). The saposin B biomarkers of the instant invention are Asn21 glycosylated forms of the peptide with 3 disulfide bonds. The two biomarkers are Asn21 (HexNAc) having a MW of 9072.44 and Asn21 (Hex$_2$HexNac$_2$deoxyhexose) having a of MW 9746.07.

```
                                        SEQ ID NO: 13
GDVCQDCIQM VTDIQTAVRT NSTFVQALVE

HVKEECDRLG PGMADICKNY ISQYSEIAIQ

MMMHMQPKEI CALVGFCDE
```

LTBP-2

Latent-transforming growth factor beta-binding protein 2 (LTBP-2) is a 1821 amino acid polypeptide (SwissProt #14767). The LTBP-2 biomarkers of the instant invention are C-terminal fragments of full-length LTBP-2 and are set forth as SEQ ID NOs: 14 and 15. The MW of SEQ ID NO: 14 includes 6 disulfide bonds.

```
MW 10028.11
                                        SEQ ID NO: 14
FEGLQAEECG ILNGCENGRC VRVREGYTCD
CFEGFQLDAA HMACVDVNEC DDLNGPAVLC
VHGYCENTEG SYRCHCSPGY VAEAGPPHCT
AKE

MW 9872.8
                                        SEQ ID NO: 15
LQAEECG ILNGCENGRC VRVREGYTCD
CFEGFQLDAA HMACVDVNEC
DDLNGPAVLC
VHGYCENTEG SYRCHCSPGY
VAEAGPPHCT AKE
```

Small MBL-Associated Protein

Small MBL-associated protein (sMAP) is a 185 amino acid polypeptide (SwissProt #O00187-2). The sMAP biomarker of the invention is a C-terminal fragment of the full length polypeptide with a MW of 5499.04 and contains 3 disulfide bonds and Asn22 is 3-hydroxyasparagine.

```
MW 5495.27
                                        SEQ ID NO: 16
EDIDECQVAPGEAPTCDHHCHNHLGGFYCS

CRAGYVLHRNKRTCSEQSL
```

Albumin

Albumin is a 609 residue polypeptide (SwissProt #P02768). The albumin marker of the instant invention comprises two albumin fragments that are connected by a disulfide bond. The biomarker comprises the peptide set forth as SEQ ID NO: 17 disulfied linked to the peptide set forth as SEQ ID NO: 18. The peptide of SEQ ID NO: 18 further comprises an intramolecular disulfide bond. The MW of the biomarker is 4355.82 daltons.

```
                                          SEQ ID NO: 17
    DKLC

SEQ ID NO: 18
    ETYGEMADCCAKQEPERNECFLQHKDDNPNLPR
```

Fibrinogen Beta

Fibrinogen beta (SwissProt #P02675) N-terminal fragment with N-terminal Gln modified to pyrrolidone carboxylic acid

```
    Mw 4417.85
                                          SEQ ID NO: 19
    QGVNDNEEGF FSARGHRPLD KKREEAPSLR PAPPPISGGG Y
```

Beta-2-Microglobulin

Beta-2-microglobuluin (SwissProt #P61769) full-length protein with one disulfide bond. MW 11729.17 Da

```
                                          SEQ ID NO: 20
    IQRTPKIQVY SRHPAENGKS NFLNCYVSGF HPSDIEVDLL

KNGERIEKVE HSDLSFSKDW SFYLLYYTEF TPTEKDEYAC

RVNHVTLSQP KIVKWDRDM
```

The preferred biological sources for detection of the biomarkers identified in Table 1 is urine. These biomarkers may also be detected in ascites fluid and cyst fluid, serum, tissues and organs such as liver, and in specific cells, such as macrophages.

3. Biomarkers and Different Forms of a Protein

Proteins frequently exist in a sample in a plurality of different forms. These forms can result from either or both of pre- and post-translational modification. Pre-translational modified forms include allelic variants, splice variants and RNA editing forms. Post-translationally modified forms include forms resulting from proteolytic cleavage (e.g., fragments of a parent protein), glycosylation, phosphorylation, lipidation, oxidation, methylation, cysteinylation, sulphonation and acetylation. When detecting or measuring a protein in a sample, the ability to differentiate between different forms of a protein depends upon the nature of the difference and the method used to detect or measure. For example, an immunoassay using a monoclonal antibody will detect all forms of a protein containing the eptiope and will not distinguish between them. However, a sandwich immunoassay that uses two antibodies directed against different epitopes on a protein will detect all forms of the protein that contain both epitopes and will not detect those forms that contain only one of the epitopes. In diagnostic assays, the inability to distinguish different forms of a protein has little impact when the forms detected by the particular method used are equally good biomarkers as any particular form. However, when a particular form (or a subset of particular forms) of a protein is a better biomarker than the collection of different forms detected together by a particular method, the power of the assay may suffer. In this case, it is useful to employ an assay method that distinguishes between forms of a protein and that specifically detects and measures a desired form or forms of the protein. Distinguishing different forms of an analyte or specifically detecting a particular form of an analyte is referred to as "resolving" the analyte.

Mass spectrometry is a particularly powerful methodology to resolve different forms of a protein because the different forms typically have different masses that can be resolved by mass spectrometry. Accordingly, if one form of a protein is a superior biomarker for a disease than another form of the biomarker, mass spectrometry may be able to specifically detect and measure the useful form where traditional immunoassay fails to distinguish the forms and fails to specifically detect to useful biomarker.

One useful methodology combines mass spectrometry with immunoassay. First, a biosepcific capture reagent (e.g., an antibody, aptamer or Affibody that recognizes the biomarker and other forms of it) is used to capture the biomarker of interest. Preferably, the biospecific capture reagent is bound to a solid phase, such as a bead, a plate, a membrane or a chip. After unbound materials are washed away, the captured analytes are detected and/or measured by mass spectrometry. (This method also will also result in the capture of protein interactors that are bound to the proteins or that are otherwise recognized by antibodies and that, themselves, can be biomarkers.) Various forms of mass spectrometry are useful for dectecting the protein forms, including laser desorption approaches, such as traditional MALDI or SELDI, and electrospray ionization.

Thus, when reference is made herein to detecting a particular protein or to measuring the amount of a particular protein, it means detecting and measuring the protein with or without resolving various forms of protein. For example, the step of "the level of one or more of the biomarkers identified in Table 1" includes measuring the one or more biomarkers by means that do not differentiate between various forms of the protein (e.g., certain immunoassays) as well as by means that differentiate some forms from other forms or that measure a specific form of the protein (e.g., hepcidin-25 and hepcidin-22, individually or in combination). In contrast, when it is desired to measure a particular form or forms of a protein, e.g., a particular form of hepcidin, the particular form (or forms) is specified. For example, "measuring hepcidin-25" means measuring hepcidin-25 in a way that distinguishes it from other forms of hepcidin, e.g., hepcidin-22.

4. Detection of Biomarkers for Ovarian Cancer

The biomarkers of this invention can be detected by any suitable method. Detection paradigms include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In one embodiment, a sample is analyzed by means of a biochip. A biochip generally comprises a solid substrate having a substantially planar surface, to which a capture reagent (also called an adsorbent or affinity reagent) is attached. Frequently, the surface of a biochip comprises a plurality of addressable locations, each of which has the capture reagent bound there.

Protein biochips are biochips adapted for the capture of polypeptides. Many protein biochips are described in the art.

These include, for example, protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK). Examples of such protein biochips are described in the following patents or published patent applications: U.S. Pat. No. 6,225,047 (Hutchens & Yip); U.S. Pat. No. 6,537,749 (Kuimelis and Wagner); U.S. Pat. No. 6,329,209 (Wagner et al.); PCT International Publication No. WO 00/56934 (Englert et al.); PCT International Publication No. WO 03/048768 (Boutell et al.) and U.S. Pat. No. 5,242,828 (Bergstrom et al.).

4.1. Detection by Mass Spectrometry

In a preferred embodiment, the biomarkers of this invention are detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these.

In a further preferred method, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer. The analyis of proteins by LDI can take the form of MALDI or of SELDI 4.1.1. SELDI A preferred mass spectrometric technique for use in the invention is "Surface Enhanced Laser Desorption and Ionization" or "SELDI," as described, for example, in U.S. Pat. No. 5,719,060 and No. 6,225,047, both to Hutchens and Yip. This refers to a method of desorption/ionization gas phase ion spectrometry (e.g., mass spectrometry) in which an analyte (here, one or more of the biomarkers) is captured on the surface of a SELDI mass spectrometry probe.

SELDI also has been called is called "affinity capture mass spectrometry" or "Surface-Enhanced Affinity Capture" ("SEAC"). This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent is attached to the probe surface by physisorption or chemisorption. In certain embodiments the probes have the capture reagent already attached to the surface. In other embodiments, the probes are pre-activated and include a reactive moiety that is capable of binding the capture reagent, e.g., through a reaction forming a covalent or coordinate covalent bond. Epoxide and acyl-imidizole are useful reactive moieties to covalently bind polypeptide capture reagents such as antibodies or cellular receptors. Nitrilotriacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitrilotriacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen Biosystems, Inc. comprise surfaces having chromatographic or biospecific adsorbents attached thereto at addressable locations. Ciphergen ProteinChip® arrays include NP20 (hydrophilic); H4 and H50 (hydrophobic); SAX-2, Q-10 and (anion exchange); WCX-2 and CM-10 (cation exchange); IMAC-3, IMAC-30 and IMAC-50 (metal chelate); and PS-10, PS-20 (reactive surface with acyl-imidizole, epoxide) and PG-20 (protein G coupled through acyl-imidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitrilotriacetic acid functionalities (IMAC 3 and IMAC 30) or O-methacryloyl-N,N-bis-carboxymethyl tyrosine funtionalities (IMAC 50) that adsorb transition metal ions, such as copper, nickel, zinc, and gallium, by chelation. Preactivated ProteinChip arrays have acyl-imidizole or epoxide functional groups that can react with groups on proteins for covalent binding.

Such biochips are further described in: U.S. Pat. No. 6,579,719 (Hutchens and Yip, "Retentate Chromatography," Jun. 17, 2003); U.S. Pat. No. 6,897,072 (Rich et al., "Probes for a Gas Phase Ion Spectrometer," May 24, 2005); U.S. Pat. No. 6,555,813 (Beecher et al., "Sample Holder with Hydrophobic Coating for Gas Phase Mass Spectrometer," Apr. 29, 2003); U.S. Patent Publication No. U.S. 2003-0032043 A1 (Pohl and Papanu, "Latex Based Adsorbent Chip," Jul. 16, 2002); and PCT International Publication No. WO 03/040700 (Um et al., "Hydrophobic Surface Chip," May 15, 2003); U.S. Patent Publication No. US 2003-0218130 A1 (Boschetti et al., "Biochips With Surfaces Coated With Polysaccharide-Based Hydrogels," Apr. 14, 2003) and U.S. Patent Publication No. U.S. 2005-059086 A1 (Huang et al., "Photocrosslinked Hydrogel Blend Surface Coatings," Mar. 17, 2005).

In general, a probe with an adsorbent surface is contacted with the sample for a period of time sufficient to allow the biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

In yet another method, one can capture the biomarkers with a solid-phase bound immuno-adsorbent that has antibodies that bind the biomarkers. After washing the adsorbent to remove unbound material, the biomarkers are eluted from the solid phase and detected by applying to a SELDI chip that binds the biomarkers and analyzing by SELDI.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

4.1.2. SEND

Another method of laser desorption mass spectrometry is called Surface-Enhanced Neat Desorption ("SEND"). SEND involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-ethoxy)silyl propyl methacrylate. In another embodiment, the composition is a co-polymer of α-cyano-4-methacryloyloxycinnamic acid and octadecyl-methacrylate ("C18 SEND"). SEND is further described in U.S. Pat. No. 6,124,137 and PCT International Publication No. WO 03/64594 (Kitagawa, "Monomers And Polymers Having Energy Absorbing Moieties Of Use In Desorption/Ionization Of Analytes," Aug. 7, 2003).

SEAC/SEND is a version of laser desorption mass spectrometry in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

4.1.3. SEPAR

Another version of LDI is called Surface-Enhanced Photolabile Attachment and Release ("SEPAR"). SEPAR involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker profile, pursuant to the present invention.

4.1.4. MALDI

MALDI is a traditional method of laser desorption/ionization used to analyte biomolecules such as proteins and nucleic acids. In one MALDI method, the sample is mixed with matrix and deposited directly on a MALDI chip. However, the complexity of biological samples such as serum or urine make this method less than optimal without prior fractionation of the sample. Accordingly, in certain embodiments with biomarkers are preferably first captured with biospecific (e.g., an antibody) or chromatographic materials coupled to a solid support such as a resin (e.g., in a spin column). Specific affinity materials that bind the biomarkers of this invention are described above. After purification on the affinity material, the biomarkers are eluted and then detected by MALDI.

4.1.5. Other Forms of Ionization in Mass Spectrometry

In another method, the biomarkers are detected by LC-MS or LC-LC-MS. This involves resolving the proteins in a sample by one or two passes through liquid chromatography, followed by mass spectrometry analysis, typically electrospray ionization.

4.1.6. Data Analysis

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's ProteinChip® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

4.1.7. General Protocol for SELDI Detection of Biomarkers for Ovarian Cancer

A preferred protocol for the detection of the biomarkers of this invention is as follows. The biological sample to be tested, e.g., urine, preferably is subject to pre-fractionation before SELDI analysis. This simplifies the sample and improves sensitivity. A preferred method of pre-fractionation involves contacting the sample with an anion exchange chromatographic material, such as Q HyperD (BioSepra, SA). The bound materials are then subject to stepwise pH elution using buffers at pH 9, pH 7, pH 5 and pH 4. Various fractions containing the biomarker are collected.

The sample to be tested (preferably pre-fractionated) is then contacted with an affinity capture probe comprising an cation exchange adsorbent (preferably a CM10 ProteinChip array (Ciphergen Biosystems, Inc.)) or an IMAC adsorbent (preferably an IMAC30 ProteinChip array (Ciphergen Biosystems, Inc.)), again as indicated in Table 1. The probe is washed with a buffer that will retain the biomarker while washing away unbound molecules. A suitable wash for each biomarker is the buffer identified in Table 1. The biomarkers are detected by laser desorption/ionization mass spectrometry.

Alternatively, samples may be diluted, with or without denaturing, in the appropriate array binding buffer and bound and washed under conditions optimized for detecting each analyte.

Alternatively, if antibodies that recognize the biomarker are available, for example from Dako, U.S. Biological, Chemicon, Abcam and Genway. These can be attached to the surface of a probe, such as a pre-activated PSI 0 or PS20 ProteinChip array (Ciphergen Biosystems, Inc.). These antibodies can capture the biomarkers from a sample onto the probe surface. Then the biomarkers can be detected by, e.g., laser desorption/ionization mass spectrometry.

Any robot that performs fluidics operations can be used in these assays, for example, those available from Hewlett Packard and Hamilton.

4.2. Detection by Immunoassay

In another embodiment of the invention, the biomarkers of the invention are measured by a method other than mass spectrometry or other than methods that rely on a measurement of the mass of the biomarker. In one such embodiment that does not rely on mass, the biomarkers of this invention are measured by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, sandwich immunoassays including ELISA or fluorescence-based immunoassays, as well as other enzyme immunoassays. Nephelometry is an assay done in liquid phase, in which antibodies are in solution. Binding of the antigen to the antibody results in changes in absorbance, which is measured. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

5. Determination of Subject Ovarian Cancer Status

The biomarkers of the invention can be used in diagnostic tests to assess ovarian cancer status in a subject, e.g., to diagnose ovarian cancer. The phrase "ovarian cancer status" includes any distinguishable manifestation of the disease, including non-disease. For example, ovarian cancer status includes, without limitation, the presence or absence of disease (e.g., ovarian cancer v. non-ovarian cancer), the risk of developing disease, the stage of the disease, the progression of disease (e.g., progress of disease or remission of disease over time) and the effectiveness or response to treatment of disease.

The correlation of test results with ovarian cancer status involves applying a classification algorithm of some kind to the results to generate the status. The classification algorithm may be as simple as determining whether or not the amount of one or more biomarkers identified in Table 1 measured is above or below a particular cut-off number. When multiple biomarkers are used, the classification algorithm may be a linear regression formula. Alternatively, the classification algorithm may be the product of any of a number of learning algorithms described herein.

In the case of complex classification algorithms, it may be necessary to perform the algorithm on the data, thereby determining the classification, using a computer, e.g., a programmable digital computer. In either case, one can then record the status on tangible medium, for example, in computer-readable format such as a memory drive or disk or simply printed on paper. The result also could be reported on a computer screen.

5.1. Single Markers

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

The biomarkers of this invention show a statistical difference in different ovarian cancer statuses. Diagnostic tests that use these biomarkers alone or in combination show a sensitivity and specificity of at least 75%, at least 80%, at least 85%, at least 90%, at least 95%, at least 98% and about 100%.

Each biomarker listed in Table 1 is differentially present in ovarian cancer, and, therefore, each is individually useful in aiding in the determination of ovarian cancer status. The method involves, first, measuring the selected biomarker in a subject sample using the methods described herein, e.g., capture on a SELDI biochip followed by detection by mass spectrometry and, second, comparing the measurement with a diagnostic amount or cut-off that distinguishes a positive ovarian cancer status from a negative ovarian cancer status. The diagnostic amount represents a measured amount of a biomarker above which or below which a subject is classified as having a particular ovarian cancer status. As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the biomarker in a statistically significant number of samples from subjects with the different ovarian cancer statuses, as was done here, and drawing the cut-off to suit the diagnostician's desired levels of specificity and sensitivity.

5.2. Combinations of Markers

While individual biomarkers are useful diagnostic biomarkers, it has been found that a combination of biomarkers can provide greater predictive value of a particular status than single biomarkers alone. Specifically, the detection of a plurality of biomarkers in a sample can increase the sensitivity and/or specificity of the test. A combination of at least two biomarkers is sometimes referred to as a "biomarker profile" or "biomarker fingerprint." Accordingly, the biomarkers of Table 1 can be combined with other biomarkers identified in Table 1, or other known biomarkers for ovarian cancer to improve the sensitivity and/or specificity of the diagnostic test.

The diagnosis of ovarian cancer typically involves the measurement of CA125, as increased levels of this marker are correlated with ovarian cancer. Therefore, levels of CA125 can be correlated with any combination of the above markers in determining ovarian cancer status.

Other biomarkers with which the biomarkers identified in Table 1 can be combined include, but are not limited to, CA125, CA125 II, CA15-3, CA19-9, CA72-4, CA 195, tumor associated trypsin inhibitor (TATI), CEA, placental alkaline phosphatase (PLAP), Sialyl TN, galactosyltransferase, macrophage colony stimulating factor (M-CSF, CSF-1), lysophosphatidic acid (LPA), 110 kD component of the extracellular domain of the epidermal growth factor receptor (p110EGFR), tissue kallikreins, e.g., kallikrein 6 and kallikrein 10 (NES-1), prostasin, HE4, creatine kinase B (CKB), LASA, HER-2/neu, urinary gonadotropin peptide, Dianon NB 70/K, Tissue peptide antigen (TPA), osteopontin, and haptoglobin, leptin, prolactin, insulin like growth factor I or II. CA125 is especially useful in that women undergoing tests for ovarian cancer typically have CA125 tested as routine part of the work-up.

5.3. Ovarian Cancer Status

Determining ovarian cancer status typically involves classifying an individual into one of two or more groups (statuses) based on the results of the diagnostic test. The diagnostic tests described herein can be used to classify between a number of different states.

5.3.1. Presence of Disease

In one embodiment, this invention provides methods for determining the presence or absence of ovarian cancer in a subject (status: ovarian cancer v. non-ovarian cancer). The presence or absence of ovarian cancer is determined by measuring the relevant biomarker or biomarkers and then either submitting them to a classification algorithm or comparing them with a reference amount and/or pattern of biomarkers that is associated with the particular risk level.

5.3.2. Determining Risk of Developing Disease

In one embodiment, this invention provides methods for determining the risk of developing ovarian cancer in a subject (status: low-risk v. high risk). Biomarker amounts or patterns are characteristic of various risk states, e.g., high, medium or low. The risk of developing a disease is determined by measuring the relevant biomarker or biomarkers and then either submitting them to a classification algorithm or comparing them with a reference amount and/or pattern of biomarkers that is associated with the particular risk level

5.3.3. Determining Stage of Disease

In one embodiment, this invention provides methods for determining the stage of disease in a subject. Each stage of the disease has a characteristic amount of a biomarker or relative amounts of a set of biomarkers (a pattern). The stage of a disease is determined by measuring the relevant biomarker or biomarkers and then either submitting them to a classification algorithm or comparing them with a reference amount and/or pattern of biomarkers that is associated with the particular stage. For example, one can classify between early stage ovarian cancer and non-ovarian cancer or among stage I ovarian cancer, stage II ovarian cancer and stage III ovarian cancer.

5.3.4. Determining Course (Progression/Remission) of Disease

In one embodiment, this invention provides methods for determining the course of disease in a subject. Disease course refers to changes in disease status over time, including disease progression (worsening) and disease regression (improvement). Over time, the amounts or relative amounts (e.g., the pattern) of the biomarkers changes. Therefore, the trend of these markers, either increased or decreased over time toward diseased or non-diseased indicates the course of the disease. Accordingly, this method involves measuring one or more biomarkers in a subject for at least two different time points, e.g., a first time and a second time, and comparing the change in amounts, if any. The course of disease is determined based on these comparisons.

5.4. Reporting the Status

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the presence or absence in a test subject of any the biomarkers of Table 1 is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

5.5. Subject Management

In certain embodiments of the methods of qualifying ovarian cancer status, the methods further comprise managing subject treatment based on the status. Such management includes the actions of the physician or clinician subsequent to determining ovarian cancer status. For example, if a physician makes a diagnosis of ovarian cancer, then a certain regime of treatment, such as prescription or administration of chemotherapy might follow. Alternatively, a diagnosis of non-ovarian cancer or non-ovarian cancer might be followed with further testing to determine a specific disease that might the patient might be suffering from. Also, if the diagnostic test gives an inconclusive result on ovarian cancer status, further tests may be called for.

6. Generation of Classification Algorithms for Qualifying Ovarian Cancer Status In some embodiments, data derived from the spectra (e.g., mass spectra or time-of-flight spectra) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", *IEEE Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. Pat. No. 6,675,104 (Paulse et al., "Method for analyzing mass spectra").

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application No. 2002 0193950 A1 (Gavin et al., "Method or analyzing mass spectra"), U.S. Patent Application No. 2003 0004402 A1 (Hitt et al., "Process for discriminating between biological states based on hidden patterns from biological data"), and U.S. Patent Application No. 2003 0055615 A1 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, or for finding new biomarkers for ovarian cancer. The classification algorithms, in turn, form the base for diagnostic tests by providing diagnostic values (e.g., cut-off points) for biomarkers used singly or in combination.

7. Compositions of Matter

In another aspect, this invention provides compositions of matter based on the biomarkers of this invention.

In one embodiment, this invention provides biomarkers of this invention in purified form. Purified biomarkers have utility as antigens to raise antibodies. Purified biomarkers also have utility as standards in assay procedures. As used herein, a "purified biomarker" is a biomarker that has been isolated from other proteins and peptdies, and/or other material from the biological sample in which the biomarker is found. The biomarkers can be isolated from biological fluids, such as urine or serum. Biomarkers may be purified using any method known in the art, including, but not limited to, mechanical separation (e.g., centrifugation), ammonium sulphate precipitation, dialysis (including size-exclusion dialysis), electrophoresis (e.g. acrylamide gel electrophoresis) size-exclusion chromatography, affinity chromatography, anion-exchange chromatography, cation-exchange chromatography, and methal-chelate chromatography. Such methods may be performed at any appropriate scale, for example, in a chromatography column, or on a biochip.

In another embodiment, this invention provides a biospecific capture reagent, optionally in purified form, that specifically binds a biomarker of this invention. In one embodiment, the biospecific capture reagent is an antibody. Such compositions are useful for detecting the biomarker in a detection assay, e.g., for diagnostics.

In another embodiment, this invention provides an article comprising a biospecific capture reagent that binds a biomarker of this invention, wherein the reagent is bound to a solid phase. For example, this invention contemplates a device comprising bead, chip, membrane, monolith or microtiter plate derivatized with the biospecific capture reagent. Such articles are useful in biomarker detection assays.

In another aspect this invention provides a composition comprising a biospecific capture reagent, such as an antibody, bound to a biomarker of this invention, the composition optionally being in purified form. Such compositions are useful for purifying the biomarker or in assays for detecting the biomarker.

In another embodiment, this invention provides an article comprising a solid substrate to which is attached an adsorbent, e.g., a chromatographic adsorbent or a biospecific capture reagent, to which is further bound a biomarker of this invention. In one embodiment, the article is a biochip or a probe for mass spectrometry, e.g., a SELDI probe. Such articles are useful for purifying the biomarker or detecting the biomarker.

8. Kits for Detection of Biomarkers for Ovarian Cancer

In another aspect, the present invention provides kits for qualifying ovarian cancer status, which kits are used to detect biomarkers according to the invention. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of biospecfic capture reagents, the kit can comprise a solid support with a reactive surface, and a container comprising the biospecific capture reagent.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

9. Determining Therapeutic Efficacy of Pharmaceutical Drug

In another embodiment, this invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of the biomarkers identified in Table 1 changes toward a non-disease profile. Therefore, one can follow the course of the amounts of these biomarkers in the subject during the course of treatment. Accordingly, this method involves measuring one or more biomarkers in a subject receiving drug therapy, and correlating the amounts of the biomarkers with the disease status of the subject. One embodiment of this method involves determining the levels of the biomarkers for at least two different time points during a course of drug therapy, e.g., a first time and a second time, and comparing the change in amounts of the biomarkers, if any. For example, the biomarkers can be measured before and after drug administration or at two different time points during drug administration. The effect of therapy is determined based on these comparisons. If a treatment is effective, then the biomarkers will trend toward normal, while if treatment is ineffective, the biomarkers will trend toward disease indications. If a treatment is effective, then the biomarkers will trend toward normal, while if treatment is ineffective, the biomarkers will trend toward disease indications.

10. Use of Biomarkers for Ovarian Cancer in Screening Assays and Methods of Treating Ovarian Cancer The methods of the present invention have other applications as well. For example, the biomarkers can be used to screen for compounds that modulate the expression of the biomarkers in vitro or in vivo, which compounds in turn may be useful in treating or preventing ovarian cancer in patients. In another example, the biomarkers can be used to monitor the response to treatments for ovarian cancer. In yet another example, the biomarkers can be used in heredity studies to determine if the subject is at risk for developing ovarian cancer.

Compounds suitable for therapeutic testing may be screened initially by identifying compounds which interact with one or more biomarkers listed herein. By way of example, screening might include recombinantly expressing a biomarker, purifying the biomarker, and affixing the biomarker to a substrate. Test compounds would then be contacted with the substrate, typically in aqueous conditions, and interactions between the test compound and the biomarker are measured, for example, by measuring elution rates as a function of salt concentration. Certain proteins may recognize and cleave one or more biomarkers of Table I, in which case the proteins may be detected by monitoring the digestion of one or more biomarkers in a standard assay, e.g., by gel electrophoresis of the proteins.

In a related embodiment, the ability of a test compound to inhibit the activity of one or more of the biomarkers may be measured. One of skill in the art will recognize that the techniques used to measure the activity of a particular biomarker will vary depending on the function and properties of the biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibit or enhance the activity of a given biomarker may be determined by measuring the rates of catalysis in the presence or absence of the test compounds. The ability of a test compound to interfere with a non-enzymatic (e.g., structural) function or activity of one or more of the biomarkers herein may also be measured.

Test compounds capable of modulating the activity of any of the biomarkers of Table I may be administered to patients who are suffering from or are at risk of developing ovarian cancer or other cancer. For example, the administration of a test compound which increases the activity of a particular biomarker may decrease the risk of ovarian cancer in a patient if the activity of the particular biomarker in vivo prevents the accumulation of proteins for ovarian cancer. Conversely, the administration of a test compound which decreases the activity of a particular biomarker may decrease the risk of ovarian cancer in a patient if the increased activity of the biomarker is responsible, at least in part, for the onset of ovarian cancer.

In an additional aspect, the invention provides a method for identifying compounds useful for the treatment of disorders such as ovarian cancer which are associated with increased levels of modified forms of the biomarkers identified in Table 1. For example, in one embodiment, cell extracts or expression libraries may be screened for compounds which catalyze the cleavage of full-length biomarkers to produce truncated forms. In one embodiment of such a screening assay, cleavage may be detected by attaching a fluorophore to hepcidin which remains quenched when the biomarker is uncleaved but which fluoresces when the protein is cleaved. Alternatively, a version of full-length biomarker modified so as to render the amide bond between amino acids x and y uncleavable may be used to selectively bind or "trap" the cellular protease which cleaves full-length biomarker at that site in vivo. Methods for screening and identifying proteases and their targets are well-documented in the scientific literature, e.g., in Lopez-Ottin et al. (Nature Reviews, 3:509-519 (2002)).

In yet another embodiment, the invention provides a method for treating or reducing the progression or likelihood of a disease. For example, after one or more proteins have been identified which cleave full-length biomarker, combinatorial libraries may be screened for compounds which inhibit the cleavage activity of the identified proteins. Methods of screening chemical libraries for such compounds are well-known in art. See, e.g., Lopez-Otin et al. (2002). Alternatively, inhibitory compounds may be intelligently designed based on the structure of the biomarkers.

At the clinical level, screening a test compound includes obtaining samples from test subjects before and after the subjects have been exposed to a test compound. The levels in the samples of one or more of the biomarkers listed in Table I may be measured and analyzed to determine whether the levels of the biomarkers change after exposure to a test compound. The samples may be analyzed by mass spectrometry, as described herein, or the samples may be analyzed by any appropriate means known to one of skill in the art. For example, the levels of one or more of the biomarkers listed in Table I may be measured directly by Western blot using radio- or fluorescently-labeled antibodies which specifically bind to the biomarkers. Alternatively, changes in the levels of mRNA encoding the one or more biomarkers may be measured and correlated with the administration of a given test compound to a subject. In a further embodiment, the changes in the level of expression of one or more of the biomarkers may be measured using in vitro methods and materials. For example, human tissue cultured cells which express, or are capable of expressing, one or more of the biomarkers of Table I may be contacted with test compounds. Subjects who have been treated with test compounds will be routinely examined for any physiological effects which may result from the treatment. In particular, the test compounds will be evaluated for their ability to decrease disease likelihood in a subject. Alternatively, if the test compounds are administered to subjects who have previously been diagnosed with ovarian cancer, test compounds will be screened for their ability to slow or stop the progression of the disease.

11. Examples

11.1. Example 1

Discovery of Biomarkers for Ovarian Cancer

It is understood that the examples and embodiments described herein are for illustrative purposes only and that various modifications or changes in light thereof will be suggested to persons skilled in the art and are to be included within the spirit and purview of this application and scope of the appended claims.

Samples:

Urine samples were acquired from the M.D. Anderson Cancer Center Ovarian cancer sample bank. The samples had been collected from cancer patients pre-operatively from years 2000 to 2006 and stored at −80° C. Sample distribution was as follows: ovarian cancer (OvCa), 237; normal, 143 and benign, 100.

Urine Profiling:

Randomized templates containing the samples to be profiled were generated using the Ciphergen Express software program. Samples from the tumor bank were thawed on ice, added to a 96 well plate (following the above mentioned template for arrangement), and centrifuged for 20 minutes at 400 rpm (urine had not been centrifuged prior to initial freezing and storage in the sample bank). Aliquots of the urine were then put into fresh 96 well plates and stored at −80° C. until use. Samples were profiled on CM10 on Mar. 14-Mar. 15, 2007 and on IMAC-Cu++ on Mar. 20-Mar. 21, 2007. Each sample was profiled (see protocol below) on duplicate ProteinChip Arrays. All replicates were prepared on the same day and were read on a PCS4000 (beginning the morning following preparation). Arrays were processed with sample using a Biomek 2000 robot.

CM10 Urine Profiling Protocol.

Add 15 µL of urine sample to 23 µL of denaturing buffer (9M urea/2% CHAPS). Incubate for 30 min at 4° C. Add 263 ul of binding buffer (BB), 100 mM Sodium Acetate pH 4, to each denatured sample. Mix well. Prepare array surface with BB washes 2×5 minutes. Remove buffer and add 150 ul of the diluted urine sample to each well. Incubate at RT with shaking for 30 minutes. Remove sample and replace with a fresh 125 ul of the same diluted sample on the appropriate spot. Incubate at RT with shaking for 30 minutes. Remove sample and wash with BB 3×5 minutes. Remove buffer and wash with H20, quickly (no incubation) 2 times. Remove bioprocessor reservoir and air dry. Add 1 ul of SPA matrix (12.5 mg/ml) in 50% acetonitrile/0.5% TFA water per spot. Air dry for 10 mins. Repeat application. Air dry overnight.

IMAC_Cu++ Urine Profiling Protocol:

Add 15 μL of urine sample to 23 μL of denaturing buffer (9M urea/2% CHAPS). Incubate for 30 min at 4° C. Add 263 ul of binding buffer (BB), 100 mM Sodium Phosphate +0.5M NaCl pH 7, to each denatured sample. Mix well. Prepare IMAC arrays with copper by adding 50 ul of 50 mM CuSO4 per well and incubate at RmT for 10 min. Wash with 150 ul/spot of water IX for 2 minutes. Incubate with 50 ul of 50 mM NaAc pH4 per spot for 5 min. Wash with water using 150 ul/spot water IX for 2 minutes. Remove water. Equilibrate IMAC30 chips 2×5 minutes with binding buffer BB. Remove buffer and add 150 ul diluted urine sample. Incubate at RT with shaking for 30 minutes. Remove sample and replace with a fresh 125 ul of the same diluted sample on the appropriate spot. Incubate at RT with shaking for 30 minutes. Remove sample and wash with BB 3×5 minutes. Remove buffer and wash with H20, quickly (no incubation) 2 times. Remove bioprocessor reservoir and air dry. Add 1 ul of SPA matrix (12.5 mg/ml) in 50% acetonitrile/0.5% TFA water per spot. Air dry for 10 mins. Repeat application. Air dry overnight.

Data Analysis:

Data were acquired using CiphergenExpress software. Mass calibration was performed using external calibrants, intensity normalization was based on total ion current using an external normalization factor, and baseline subtraction was performed. Peak detection was performed in CiphergenExpress using the criteria that a peak must have a signal/noise ratio of 3:1 and be present in 20% of the spectra. Statistical analysis was performed in CiphergenExpress using the Mann-Whitney test (for two groups, e.g. benign versus ovarian cancer) or Kruskal-Wallis test (for multiple group comparison, e.g. benign versus ovarian cancer vs normal cancer).

Identified markers are set forth in Table 1.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for diagnosing ovarian cancer in a subject comprising:
   (a) measuring in a urine sample from the subject Small MBL-associated protein C-terminal fragment (sMAP), and
   (b) correlating the measurement with ovarian cancer, wherein an elevated level of sMAP as compared to the level of sMAP from a reference subject that does not have ovarian cancer indicates the subject has ovarian cancer, thereby diagnosing ovarian cancer in the subject.

2. The method of claim 1, wherein sMAP is measured by mass spectrometry.

3. The method of claim 2, wherein mass spectrometry is SELDI-MS.

4. The method of claim 1, wherein sMAP is measured by immunoassay.

5. The method of claim 1, wherein the correlating is performed by executing a software classification algorithm.

6. The method of claim 1, further comprising: (c) reporting the diagnosis to the subject.

7. The method of claim 1, further comprising: recording the diagnosis on a tangible medium.

8. The method of claim 1, further comprising: (c) managing subject treatment based on the diagnosis.

9. The method of claim 8, further comprising: (d) measuring sMAP after subject management and correlating the measurement with disease progression.

* * * * *

SEQUENCE LISTING

<160> NUMBER OF SEQ ID NOS: 20

<210> SEQ ID NO 1
<211> LENGTH: 25
<212> TYPE: PRT
<213> ORGANISM: Homo sapiens

<400> SEQUENCE: 1

Asp Thr His Phe Pro Ile Cys Ile Phe Cys Cys Gly Cys Cys His Arg
 1               5                  10                  15

Ser Lys Cys Gly Met Cys Cys Lys Thr
            20                  25

<210> SEQ ID NO 2
<211> LENGTH: 22
<212> TYPE: PRT
<213> ORGANISM: Homo sapiens

<400> SEQUENCE: 2

Phe Pro Ile Cys Ile Phe Cys Cys Gly Cys Cys His Arg Ser Lys Cys
 1               5                  10                  15

Gly Met Cys Cys Lys Thr
            20

<210> SEQ ID NO 3
<211> LENGTH: 76
<212> TYPE: PRT
<213> ORGANISM: Homo sapiens

<400> SEQUENCE: 3

Met Gln Ile Phe Val Lys Thr Leu Thr Gly Lys Thr Ile Thr Leu Glu
 1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 4
<211> LENGTH: 73
<212> TYPE: PRT
<213> ORGANISM: Homo sapiens

<400> SEQUENCE: 4

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu
65                  70

<210> SEQ ID NO 5
<211> LENGTH: 72
<212> TYPE: PRT
<213> ORGANISM: Homo sapiens

<400> SEQUENCE: 5

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg
65                  70

<210> SEQ ID NO 6
<211> LENGTH: 44
<212> TYPE: PRT
<213> ORGANISM: Homo sapiens

<400> SEQUENCE: 6

Leu Thr Gly Leu Gly His Arg Ser Asp His Tyr Asn Cys Val Ser Ser
1               5                   10                  15

Gly Gly Gln Cys Leu Tyr Ser Ala Cys Pro Ile Phe Thr Lys Ile Gln
            20                  25                  30

Gly Thr Cys Tyr Arg Gly Lys Ala Lys Cys Cys Lys
        35                  40

<210> SEQ ID NO 7
<211> LENGTH: 29
<212> TYPE: PRT
<213> ORGANISM: Homo sapiens

<400> SEQUENCE: 7

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25

```
<210> SEQ ID NO 8
<211> LENGTH: 30
<212> TYPE: PRT
<213> ORGANISM: Homo sapiens

<400> SEQUENCE: 8

Ala Cys Tyr Cys Arg Ile Pro Ala Cys Ile Ala Gly Glu Arg Arg Tyr
  1               5                  10                  15

Gly Thr Cys Ile Tyr Gln Gly Arg Leu Trp Ala Phe Cys Cys
             20                  25                  30

<210> SEQ ID NO 9
<211> LENGTH: 49
<212> TYPE: PRT
<213> ORGANISM: Homo sapiens

<400> SEQUENCE: 9

Glu Asp Ile Asp Glu Cys Gln Val Ala Pro Gly Glu Ala Pro Thr Cys
  1               5                  10                  15

Asp His His Cys His Asn His Leu Gly Gly Phe Tyr Cys Ser Cys Arg
             20                  25                  30

Ala Gly Tyr Val Leu His Arg Asn Lys Arg Thr Cys Ser Glu Gln Ser
         35                  40                  45

Leu

<210> SEQ ID NO 10
<211> LENGTH: 56
<212> TYPE: PRT
<213> ORGANISM: Homo sapiens

<400> SEQUENCE: 10

Asp Ser Leu Gly Arg Glu Ala Lys Cys Tyr Asn Glu Leu Asn Gly Cys
  1               5                  10                  15

Thr Lys Ile Tyr Asp Pro Val Cys Gly Thr Asp Gly Asn Thr Tyr Pro
             20                  25                  30

Asn Glu Cys Val Leu Cys Phe Glu Asn Arg Lys Arg Gln Thr Ser Ile
         35                  40                  45

Leu Ile Gln Lys Ser Gly Pro Cys
     50                  55

<210> SEQ ID NO 11
<211> LENGTH: 81
<212> TYPE: PRT
<213> ORGANISM: Homo sapiens

<400> SEQUENCE: 11

Leu Lys Cys Tyr Thr Cys Lys Glu Pro Met Thr Ser Ala Ser Cys Arg
  1               5                  10                  15

Thr Ile Thr Arg Cys Lys Pro Glu Asp Thr Ala Cys Met Thr Thr Leu
             20                  25                  30

Val Thr Val Glu Ala Glu Tyr Pro Phe Asn Gln Ser Pro Val Val Thr
         35                  40                  45

Arg Ser Cys Ser Ser Ser Cys Val Ala Thr Asp Pro Asp Ser Ile Gly
     50                  55                  60

Ala Ala His Leu Ile Phe Cys Cys Phe Arg Asp Leu Cys Asn Ser Glu
 65                  70                  75                  80

Leu
```

```
<210> SEQ ID NO 12
<211> LENGTH: 106
<212> TYPE: PRT
<213> ORGANISM: Homo sapiens

<400> SEQUENCE: 12

Glu Lys Pro Ser Pro Cys Gln Cys Ser Arg Leu Ser Pro His Asn Arg
 1               5                  10                  15

Thr Asn Cys Gly Phe Pro Gly Ile Thr Ser Asp Gln Cys Phe Asp Asn
             20                  25                  30

Gly Cys Cys Phe Asp Ser Ser Val Thr Gly Val Pro Trp Cys Phe His
         35                  40                  45

Pro Leu Pro Lys Gln Glu Ser Asp Gln Cys Val Met Glu Val Ser Asp
 50                  55                  60

Arg Arg Asn Cys Gly Tyr Pro Gly Ile Ser Pro Glu Gly Cys Ala Ser
 65                  70                  75                  80

Arg Lys Cys Cys Phe Ser Asn Phe Ile Phe Glu Val Pro Trp Cys Phe
                 85                  90                  95

Phe Pro Lys Ser Val Glu Asp Cys His Tyr
             100                 105

<210> SEQ ID NO 13
<211> LENGTH: 79
<212> TYPE: PRT
<213> ORGANISM: Homo sapiens

<400> SEQUENCE: 13

Gly Asp Val Cys Gln Asp Cys Ile Gln Met Val Thr Asp Ile Gln Thr
 1               5                  10                  15

Ala Val Arg Thr Asn Ser Thr Phe Val Gln Ala Leu Val Glu His Val
             20                  25                  30

Lys Glu Glu Cys Asp Arg Leu Gly Pro Gly Met Ala Asp Ile Cys Lys
         35                  40                  45

Asn Tyr Ile Ser Gln Tyr Ser Glu Ile Ala Ile Gln Met Met Met His
 50                  55                  60

Met Gln Pro Lys Glu Ile Cys Ala Leu Val Gly Phe Cys Asp Glu
 65                  70                  75

<210> SEQ ID NO 14
<211> LENGTH: 93
<212> TYPE: PRT
<213> ORGANISM: Homo sapiens

<400> SEQUENCE: 14

Phe Glu Gly Leu Gln Ala Glu Cys Gly Ile Leu Asn Gly Cys Glu
 1               5                  10                  15

Asn Gly Arg Cys Val Arg Val Arg Glu Gly Tyr Thr Cys Asp Cys Phe
             20                  25                  30

Glu Gly Phe Gln Leu Asp Ala Ala His Met Ala Cys Val Asp Val Asn
         35                  40                  45

Glu Cys Asp Asp Leu Asn Gly Pro Ala Val Leu Cys Val His Gly Tyr
 50                  55                  60

Cys Glu Asn Thr Glu Gly Ser Tyr Arg Cys His Cys Ser Pro Gly Tyr
 65                  70                  75                  80

Val Ala Glu Ala Gly Pro Pro His Cys Thr Ala Lys Glu
                 85                  90

<210> SEQ ID NO 15
<211> LENGTH: 90
```

```
<212> TYPE: PRT
<213> ORGANISM: Homo sapiens

<400> SEQUENCE: 15

Leu Gln Ala Glu Glu Cys Gly Ile Leu Asn Gly Cys Glu Asn Gly Arg
 1               5                  10                  15

Cys Val Arg Val Arg Glu Gly Tyr Thr Cys Asp Cys Phe Glu Gly Phe
                20                  25                  30

Gln Leu Asp Ala Ala His Met Ala Cys Val Asp Val Asn Glu Cys Asp
            35                  40                  45

Asp Leu Asn Gly Pro Ala Val Leu Cys Val His Gly Tyr Cys Glu Asn
        50                  55                  60

Thr Glu Gly Ser Tyr Arg Cys His Cys Ser Pro Gly Tyr Val Ala Glu
 65                 70                  75                  80

Ala Gly Pro Pro His Cys Thr Ala Lys Glu
                85                  90

<210> SEQ ID NO 16
<211> LENGTH: 49
<212> TYPE: PRT
<213> ORGANISM: Homo sapiens

<400> SEQUENCE: 16

Glu Asp Ile Asp Glu Cys Gln Val Ala Pro Gly Glu Ala Pro Thr Cys
 1               5                  10                  15

Asp His His Cys His Asn His Leu Gly Gly Phe Tyr Cys Ser Cys Arg
                20                  25                  30

Ala Gly Tyr Val Leu His Arg Asn Lys Arg Thr Cys Ser Glu Gln Ser
            35                  40                  45

Leu

<210> SEQ ID NO 17
<211> LENGTH: 4
<212> TYPE: PRT
<213> ORGANISM: Homo sapiens

<400> SEQUENCE: 17

Asp Lys Leu Cys
 1

<210> SEQ ID NO 18
<211> LENGTH: 33
<212> TYPE: PRT
<213> ORGANISM: Homo sapiens

<400> SEQUENCE: 18

Glu Thr Tyr Gly Glu Met Ala Asp Cys Cys Ala Lys Gln Glu Pro Glu
 1               5                  10                  15

Arg Asn Glu Cys Phe Leu Gln His Lys Asp Asp Asn Pro Asn Leu Pro
                20                  25                  30

Arg

<210> SEQ ID NO 19
<211> LENGTH: 41
<212> TYPE: PRT
<213> ORGANISM: Homo sapiens

<400> SEQUENCE: 19

Gln Gly Val Asn Asp Asn Glu Glu Gly Phe Phe Ser Ala Arg Gly His
 1               5                  10                  15
```

```
-continued

Arg Pro Leu Asp Lys Lys Arg Glu Glu Ala Pro Ser Leu Arg Pro Ala
             20                  25                  30

Pro Pro Pro Ile Ser Gly Gly Tyr
             35              40

<210> SEQ ID NO 20
<211> LENGTH: 99
<212> TYPE: PRT
<213> ORGANISM: Homo sapiens

<400> SEQUENCE: 20

Ile Gln Arg Thr Pro Lys Ile Gln Val Tyr Ser Arg His Pro Ala Glu
 1               5                  10                  15

Asn Gly Lys Ser Asn Phe Leu Asn Cys Tyr Val Ser Gly Phe His Pro
             20                  25                  30

Ser Asp Ile Glu Val Asp Leu Leu Lys Asn Gly Glu Arg Ile Glu Lys
             35                  40                  45

Val Glu His Ser Asp Leu Ser Phe Ser Lys Asp Trp Ser Phe Tyr Leu
     50                  55                  60

Leu Tyr Tyr Thr Glu Phe Thr Pro Thr Glu Lys Asp Glu Tyr Ala Cys
 65              70                  75                  80

Arg Val Asn His Val Thr Leu Ser Gln Pro Lys Ile Val Lys Trp Asp
             85                  90                  95

Arg Asp Met
```